United States Patent [19]

Heiney, III et al.

[11] 4,222,026
[45] Sep. 9, 1980

[54] EXHAUST GAS SENSOR HAVING TWO TITANIA CERAMIC ELEMENTS

[75] Inventors: Elmer T. Heiney, III, Huntington Woods; Stanley R. Merchant; Wells L. Green, both of Garden City, all of Mich.

[73] Assignee: Ford Motor Company, Dearborn, Mich.

[21] Appl. No.: 5,426

[22] Filed: Jan. 22, 1979

[51] Int. Cl.$^3$ .............................................. H01L 7/00
[52] U.S. Cl. ..................................... 338/34; 73/27 R; 324/65 P; 338/229
[58] Field of Search ........................... 338/34, 28, 229; 324/65 P; 73/27 R; 29/610, 612, 613, 619; 422/98; 23/232 E

[56] References Cited

U.S. PATENT DOCUMENTS

| | | | |
|---|---|---|---|
| 3,639,132 | 2/1972 | Egerton et al. | 106/39 R |
| 3,886,785 | 6/1975 | Stadler et al. | 73/27 R X |
| 3,932,246 | 1/1976 | Stadler et al. | 73/27 R X |
| 4,007,435 | 2/1977 | Tien | 338/34 |

FOREIGN PATENT DOCUMENTS 2280057  2/1976  France ...................................... 338/28

*Primary Examiner*—C. L. Albritton
*Attorney, Agent, or Firm*—Robert W. Brown; Clifford L. Sadler

[57] ABSTRACT

An improved exhaust gas sensor of the type having first and second titania ceramic elements which have electrical resistances varying as a function of both the temperature and the composition of exhaust gases from internal combustion engines to which the elements are exposed. The first and second titania elements are connected in series circuit in the utilization of the sensor and the resistance of the second element over the operating temperature range of the exhaust gas sensor compensates the signal of the first titania element in a manner that produces a desired signal. The desired signal is a result of variation of the second titania element resistance values when exhaust gases cycle between lean-mixture and rich-mixture compositions. The resistance values of the second titania element are intermediate the corresponding resistances of the first titania element over the temperature range.

The second titania element is more dense than the first titania element. It has a density in the range from 3.2 g/cm$^3$ to 3.8 g/cm$^3$, i.e., between about 76% and 90% of theoretical density.

2 Claims, 8 Drawing Figures

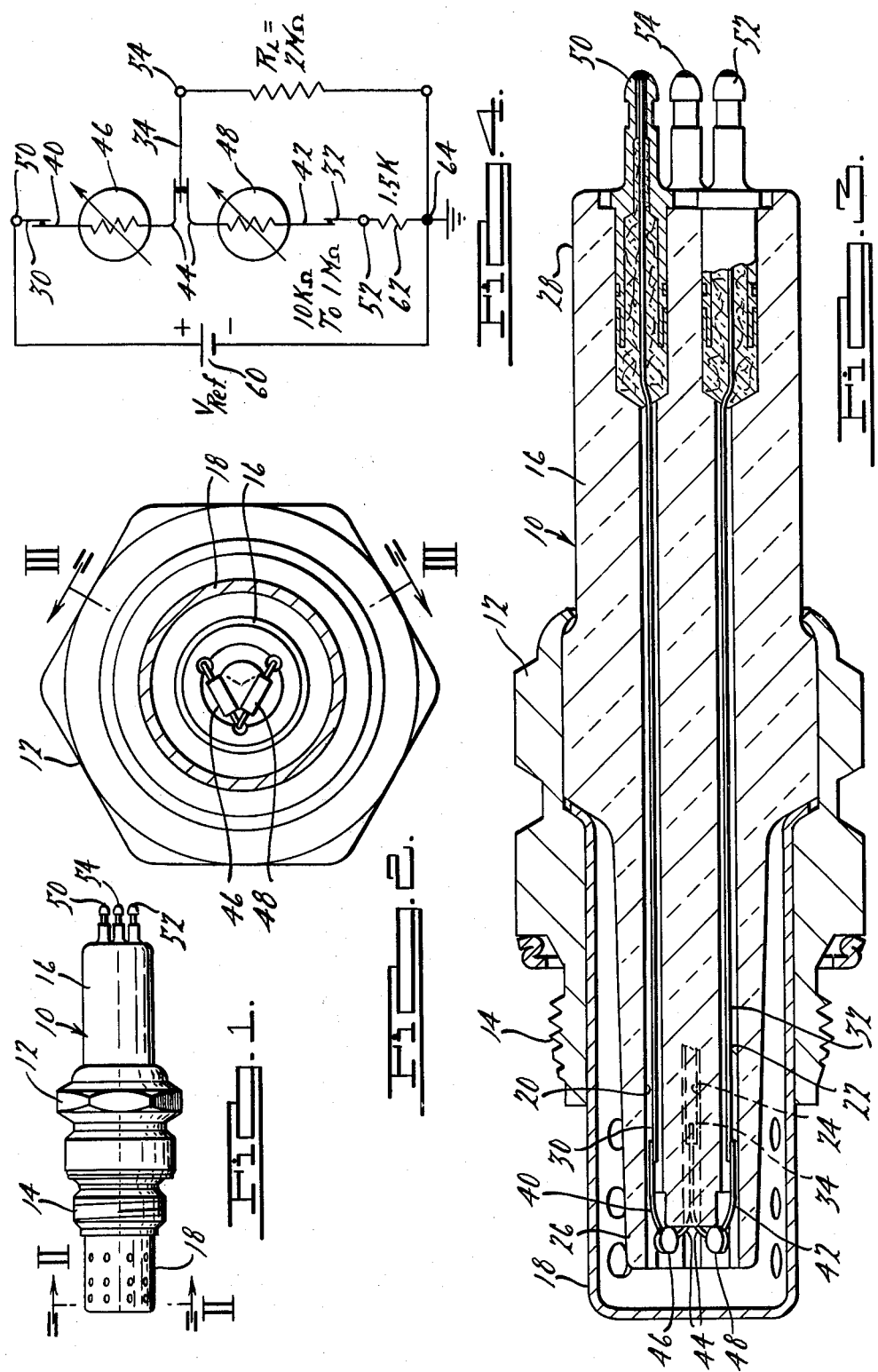

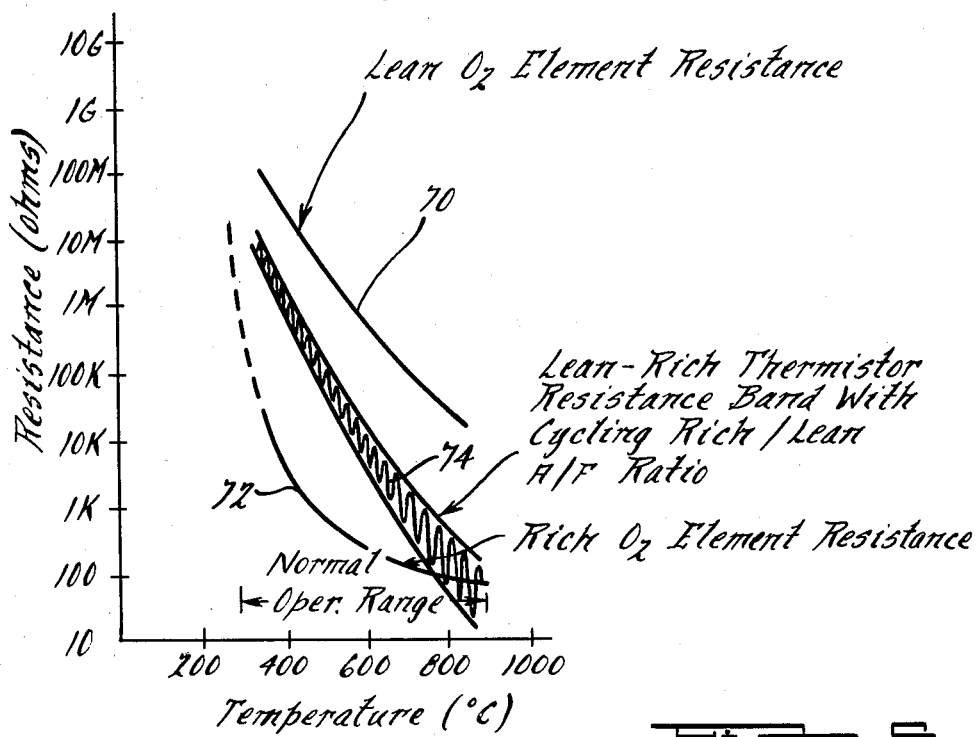
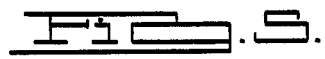
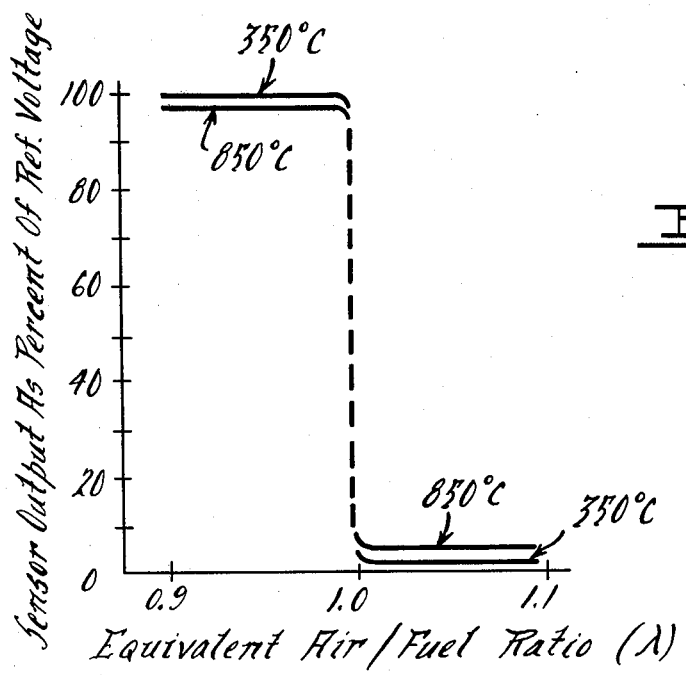

EXHAUST GAS SENSOR HAVING TWO TITANIA CERAMIC ELEMENTS

CROSS REFERENCE TO RELATED PATENTS

This invention relates to U.S. patent application Ser. No. 839,700 filed Oct. 6, 1977 in the names of S. R. Merchant et al and entitled "Titania Thermistor and Method of Fabricating". In this prior patent application, a thermistor of titania composition is disclosed having a density preferably approaching the theoretical density of titania. The present invention also is related to commonly assigned and concurrently filed U.S. patent application Ser. No. 5,422, filed in the names of E. T. Heiney and S. R. Merchant, two of the present inventors, and entitled "Exhaust Gas Sensor Electrical Circuit Improvement."

BACKGROUND

This invention relates to an improved exhaust gas sensor of the type having first and second titania ceramic elements. The titania elements have electrical resistances which vary as a function both of temperature, over the temperature range from about 350° C. to about 850° C., and the partial pressure of oxygen in exhaust gases produced by the combustion of a rich or lean (with respect to stoichiometry) air/fuel mixture.

The first and second titania elements are metal oxide ceramic materials that in use in the exhaust gas sensor are electrically connected in series. The first titania element is more responsive to the partial pressure of oxygen in the exhaust gases than is the second element, but both are responsive to variations in their temperature.

The preferred form of the first titania element is a material which is quite porous, that is, it may have a density of about 2.8 g/cm$^3$ or less, which is equal to approximately 70% of theoretical density, which is about 4.20 g/cm$^3$. Of course, the density of the first titania element may be varied to a considerable extent in this porosity range and still retain adequate response characteristics, both with respect to time and resistance. The first titania element, however, does have a resistance when subjected to lean-mixture exhaust gases and at element temperatures within the aforementioned temperature range that are about three orders of magnitude greater than the resistances thereof at corresponding temperatures when subjected to rich-mixture exhaust gases.

In the utilization of the series circuit arrangement for the titania elements in the exhaust gas sensor, it previously was thought that the second titania element or "thermistor" should have a density as close to the theoretical density as possible and, preferably, greater than 97% thereof. It now has been found that considerably improved results are achieved, at least under certain circumstances, if the thermistor or second titania element has a density other than a value approaching its theoretical density.

When the exhaust gas sensor is exposed to temperatures in the upper portion of its operating temperature range, i.e., at temperatures at about 850° C., and when the sensor is exposed for an abnormally long period of time to exhaust gases produced by the combustion of rich air/fuel mixtures, the resistance of the second titania element in the exhaust gas sensor circuit is substantially reduced and approaches that of the first titania element, which is more responsive to the partial pressure of oxygen in the exhaust gases. Thereafter, upon rapid cooling of the exhaust gas sensor, and particularly its second titania element or thermistor, the resistance thereof tends to increase only slightly. Then, if the air/fuel mixture becomes lean so that there is an excess of oxygen in the exhaust gases to which the thermistor is exposed, the thermistor resistance may not change sufficiently to produce the desired exhaust gas sensor output signal representative of the presence of a subsequently occurring rich air/fuel mixture. This can cause errors in the operation of the feedback fuel control system with which the exhaust gas sensor is used in association with the internal combustion engine of a motor vehicle.

SUMMARY OF THE INVENTION

In accordance with the invention, an improved exhaust gas sensor of the type having first and second titania ceramic elements is provided to overcome the aforementioned difficulty. Also, improved operation of the sensor throughout its operating temperature range beginning at about 350° C. is achieved and the prior art upper limit of about 700° C. is extended. In this temperature range, the first and second titania ceramic elements have electrical resistances which vary as a function of their temperature, and also as a function of the partial pressure of oxygen in exhaust gases produced by the combustion of a rich or lean (with respect to stoichiometry) air/fuel mixture to which the first and second titania elements are exposed.

The first and second titania elements have electrodes that are interconnected and adapted for receipt of an externally supplied voltage, thereby to permit an output electrical signal to be measured or sensed across one of the titania elements. The first titania element has a resistance, when subjected to lean-mixture exhaust gases and over the aforementioned temperature range, that is about three orders of magnitude, more or less, than the resistance at corresponding temperatures when it is subjected to rich-mixture exhaust gases. The second titania element has, over the temperature range and when subjected to cycling rich-mixture/lean-mixture exhaust gases, a resistance which is intermediate the respective lean-mixture and rich-mixture exhaust gas resistances of the first titania element at corresponding temperatures. Also, the second titania element has a density between about 3.2 g/cm$^3$ and about 3.8 g/cm$^3$.

The invention may be better understood by reference to the detailed description which follows and to the drawings.

BRIEF DESCRIPTION OF THE DRAWINGS

FIG. 1 is an elevational view of a titania exhaust gas oxygen sensor suitable for installation in the intake manifold of an internal combustion engine;

FIG. 2 is a sectional end view, taken along the line II—II in FIG. 1, and is shown in enlarged scale;

FIG. 3, is a sectional view, taken along the line III—III of FIG. 2, showing the internal structure of the sensor of FIGS. 1 and 2, also on an enlarged scale;

FIG. 4 is a circuit diagram illustrating the manner in which the titania oxygen sensing element and the titania thermistor shown in FIGS. 1 through 3 are electrically connected with circuitry designed to receive the sensor output voltage;

FIG. 5 is a graph of both the oxygen sensor element and titania thermistor element resistances (calculated from voltage measurements made in the circuit of FIG. 4) as a function of temperature over the operating temperature range from about 300° C. to about 900° C.;

FIG. 6 is a graph of sensor output voltage as a percent of the input (reference) voltage versus equivalent air/fuel ratio;

DETAILED DESCRIPTION

Figure 7:
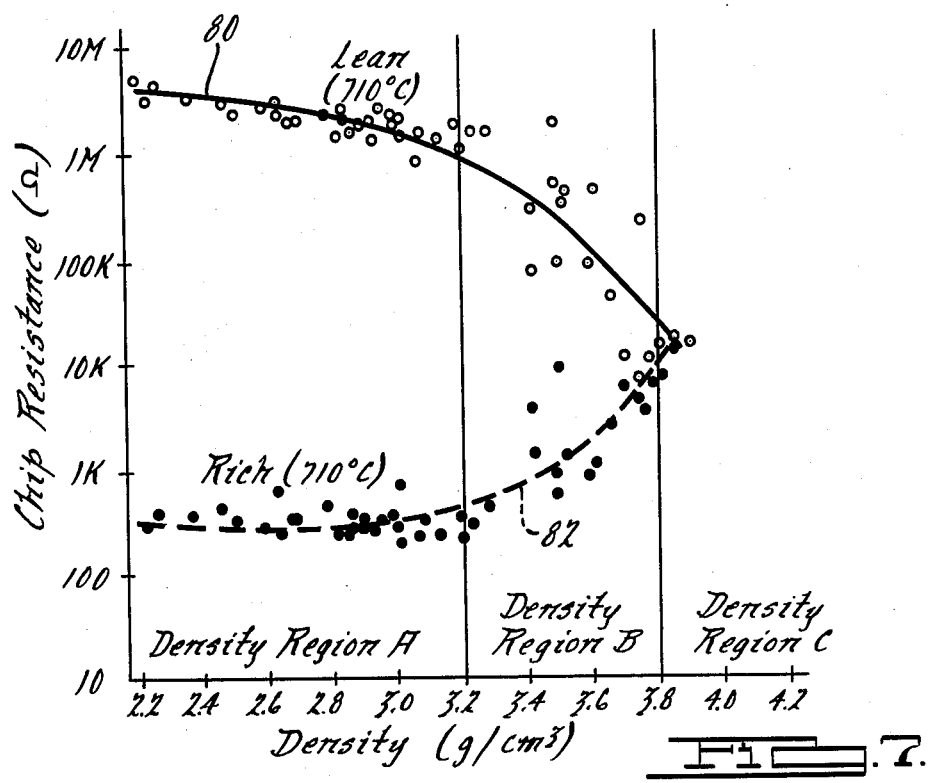
FIG. 7 is a graph illustrating the resistance of the exhaust gas sensor titania material at 710° C. as a function of its density in g/cm$^3$ following exposure of the material to rich and lean-mixture exhaust gases.

With particular reference now to FIGS. 1 through 3, wherein like numerals refer to like parts in the several views, there is shown a complete titania exhaust gas sensor assembly generally designated by the numeral 10. The sensor 10 includes a steel body 12, which may be substantially identical to a typical spark plug body, having a threaded portion 14 for engagement with a suitably threaded aperture provided within the exhaust system of an internal combustion engine (not shown). In most cases, the sensor 10 would be installed in an aperture at a location in the exhaust manifold or conduit near the flange that would connect to an exhaust pipe. A ceramic insulator 16 extends through the body 12 and has a tapered portion 26 projecting outwardly from the body 12 into the volume defined by the boundaries of a perforated protection tube 18. There are three longitudinal passages 20, 22 and 24 extending from the projecting end 26 of the ceramic insulator to its opposite end 28. Wires 30, 32 and 34 are located in the respectively corresponding passages 20, 22 and 24 and are of a heat resistant character, preferably being made from an alloy such as 80% nickel-20% chromium wire. These electrically conductive wires are welded to precious metal wire leads 40, 42 and 44 which are embedded in disc-shaped ceramic elements 46 and 48.

Element 46 is a ceramic titania O$_2$ sensor responsive to the partial pressure of oxygen in the gaseous medium to which this element is exposed. Sensor element 46 may be fabricated in accordance with the teachings of commonly assigned U.S. Pat. Nos. 3,886,785 issued June 3, 1975, and 3,932,246 issued Jan. 13, 1976, both in the names of Stadler et al. With regard to the fabrication of the oxygen sensing element 46, it is suggested that consideration be given to the teachings of commonly assigned and previously or concurrently filed patents, relating to exhaust gas sensors, expected to issue subsequent to the filing date of this patent application.

The element 48 is a titania "thermistor". The thermistor is made from titania ceramic material of greater density than the density of the more porous titania oxygen sensor 46. The thermistor 48 is intended to provide temperature compensation in accordance with the improved exhaust gas sensor electrical circuit illustrated in FIG. 4, and is intended according to the present invention to be substantially less responsive to variations in the partial pressure of oxygen in the gaseous medium to which it is exposed than is the titania oxygen sensing element 46. The oxygen sensing element 46 also could be regarded as a thermistor, but is and has not been referred to as such either herein or elsewhere.

The sensor of FIGS. 1 through 3 is intended to be used in conjunction with electronic circuitry for closed-loop feedback control of the amount of fuel supplied to an internal combustion engine. The sensor indicates whether the exhaust gases contain a substantial amount of HC and CO, or whether instead there is a substantial amount of oxygen, thereby indicating whether or not the air/fuel ratio of the mixture supplied to the engine was rich or lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio therefore is represented as 1.0 in accordance with well known practice.

The exhaust gas sensor 10 has identical terminals 50, 52 and 54 designed for connection to external circuitry as specified above to enable it to be used in a feedback fuel control system. With particular reference now to FIG. 4, there is shown a circuit that schematically represents the manner in which the sensor 10 is utilized in association with such external circuitry. The exhaust gas sensor circuitry shown in FIG. 4 embodies an improvement over prior art circuitry as is described in the aforementioned U.S. patent application Serial No. entitled "Exhaust Gas Sensor Electrical Circuit Improvement".

In FIG. 4, a DC source of regulated reference voltage 60 has its positive terminal connected to terminal 50 of the titania oxygen responsive element 46. The lead wires 40, 42 and 44 from the sensor 46 and titania thermistor 48 are welded or otherwise joined, respectively, to lead wires 30, 32 and 34 to interconnect the two ceramic elements 46 and 48 as shown. The thermistor element 48 is connected through a response-shaping resistor 62 to ground potential at 64. The output voltage of the sensor 10 is taken between the sensor terminal 54 and ground potential. This signal is applied across the input impedance or load resistance $R_L$ (about two megohms) of the engine control electronic circuitry. The term "thermistor" as used herein is somewhat of a misnomer as applied to the titania element 48 because this element has a resistance variation in its operating range from about 350° C. to 850° C. that not only is a function of its temperature, but that also is a function of the partial pressure of oxygen in exhaust gases to which it is exposed. However, it is less responsive to oxygen partial pressure than is the more porous and less dense element 46.

The input voltage to the circuit of FIG. 4 is obtained from the source reference 60 and is applied across the voltage divider comprising the series-connected variable resistances of oxygen sensor 46 and thermistor 48 in series with the response-shaping resistor 62. The output voltage of the improved exhaust gas sensor circuitry will be considered as being the voltage between the ground lead of the source of electrical energy 60 and the junction formed between the thermistor 48 and the oxygen sensing element 46. This is the voltage across the resistance $R_L$. Resistor 62 has a positive temperature coefficient in contrast to the negative temperature coefficients of the titania ceramic elements 46 and 48.

The resistance values of both the oxygen sensor 46 and the thermistor 48 vary as a function of temperature and the partial pressure of oxygen in exhaust gases produced by the combustion of air/fuel mixtures both rich and lean with respect to stoichiometry. As a result, the voltage dividing effect provides an output voltage across the load resistance $R_L$ that is substantially independent of temperature. The oxygen sensor 46, however, has a resistance which varies not only with temperature, but also (more than the thermistor element 48) with the partial pressure of oxygen in the gaseous medium to which the sensor is exposed. An increase in the resistance of the oxygen sensor 46 causes the output voltage across the load $R_L$ to decrease, and a reduction in the resistance of the oxygen sensor causes a corresponding increase in the output voltage across the resistance $R_L$. Otherwise stated, an increase in oxygen content in the engine exhaust gases (particularly a change from rich to lean in the air/fuel mixture supplied to the engine) surrounding the oxygen sensing device 46 causes its resistance to increase and thereby causes a reduction in the voltage across the load resistance $R_L$. A decrease in the oxygen content of the engine exhaust gases (change from lean to rich air/fuel mixture supplied to the engine) causes the resistance of the titania oxygen sensing element 46 to decrease in a corresponding manner and this causes an increase in the voltage across the load resistance $R_L$.

Titanium dioxide (titania) is a material that occurs naturally in mixture with other minerals. The titania is obtained by precipitation from a solution of minerals that include titania. When thus obtained by precipitation, the titania has an anatase crystal structure. When the titania material in this crystal structure is formed into an exhaust gas oxygen sensor, it is first thermally treated in a manner that allows the crystal structure to change from anatase to rutile. An increase in the temperature of the rutile material above room temperature induces oxygen vacancies into the crystal structure. This results in ionization of the titanium atoms interstitially located in the crystal structure. The concentration of the interstitial titanium ions and oxygen vacancies increase as temperature rises, and these variations in concentration are of considerable significance in the use of the titania as a sensor material. The titania oxygen sensor 46 is deliberately made considerably more porous than is the titania thermistor 48. This considerably increases (slows down) the time rate of response of the thermistor 48, as compared to that of the oxygen sensing element 46. For this reason, cyclical air/fuel mixture variations from rich to lean and from lean to rich, with respect to stoichiometry, at the frequencies occurring in feedback fuel control systems for internal combustion engines, produce little variation in the thermistor response to the resulting exhaust gases.

The curve 70 in FIG. 5 represents the resistance of the titania oxygen sensing element 46 when located in the exhaust gases emanating from an engine supplied with a lean mixture, and the curve 72 when the engine is supplied with a rich mixture. Curve 74 illustrates the resistance of the thermistor 48 as a function of temperature. The curve 74 is of alternating character indicating the small variation of the thermistor resistance that occurs as the air/fuel ratio supplied to the engine oscillates back and forth about stoichiometry. From curve 74, it is quite evident that there is but very minor variation in the resistance of the thermistor 48 as a function of the cycling oxygen content in the gaseous medium surrounding the sensor. This is much in contrast to the curves 70 and 72 representing, respectively, the lean and rich resistance values over the normal operating range of exhaust gas sensor 10. Of course, the actual resistance values for the oxygen sensing element 46 would vary back and forth between the curves 70 and 72 as the air/fuel ratio supplied to the engine is varied about stoichiometry. At the left side of the graph of FIG. 5, it may be seen that the curves 70 and 72 come together at low temperatures. This indicates that titania is not responsive to the surrounding oxygen concentration at low temperatures.

If it is assumed that a titania device, such as either of elements 46 and 48, is located in an environment in which the oxygen concentration is constant and only the temperature varies, then the number of vacancies in the titania structure may change due to thermal energy. However, the titanium atom, in those titanium oxide molecules having but one oxygen atom, have only two of their four valence electrons covalently bonded with oxygen. As the temperature of the titania increases, the thermal energy supplied to the molecules in the structure increases and the oxygen vacancies therein have greater mobility. As the oxygen deficiency or concentration of Ti interstitials increases, more electrons become available for the conduction process, and the resistivity of the material decreases. The conductivity of the titania increases or, otherwise stated, its resistance decreases as a function of temperature, as is indicated in FIG. 5 for both the thermistor element 48 and oxygen sensor element 46.

If it is now assumed that a sensor element 46 of titania is positioned in an environment of varying oxygen partial pressure, and that it is at a temperature within the titania operating range, for example, 600° C., then the number of vacancies in titania increases or decreases as a function of oxygen partial pressure.

If a titania oxygen sensor 46 is positioned in the exhaust stream of an internal combustion engine, and if the air/fuel mixture supplied to such engine continually varies between lean and rich with respect to stoichiometry, the partial pressure of oxygen to which the sensor is exposed varies cyclically. When the mixture is lean, there is an excess of oxygen in the exhaust gas and few oxidizable carbon compounds. The titania element 46 has a relatively high resistance, on the order of about 0.5 megohms. This is because oxygen from the exhaust gases will have been adsorbed on the surface of the titania element. The adsorbed oxygen atoms on the titania surface annihilate oxygen vacancies and interstitial titanium ions and migrate into the titania crystal structure. In an oxygen deficient oxide, both oxygen vacancies and interstitial ions may be involved in an equilibrium reaction with oxygen in the surrounding environment. In this equilibrium reaction, the partial pressure of oxygen in the environment determines whether the interstitial ions or the oxygen vacancies play the predominant role in the oxygen transfer process. In both cases, there is an acquisition of electrons followed by an annihilation of a vacancy. The electrons at low sensor operating temperatures are provided by charge transfer particles on the $TiO_2$, an electrical conductor having a "pool" of available electrons. At higher temperatures, thermal energy is sufficient to provide electrons required at the titania surface for the process of vacancy annihilation.

The lower the number of vacancies in the titania crystal structure, the higher is its electrical resistance. On the other hand, the more vacancies that are created in the crystal structure, the lower is the titania resistance.

When the exhaust gases change from lean-to-rich (L-R), a percentage of the oxygen atoms in the titania structure are removed to create additional vacancies. The oxygen leaves the titania crystal structure probably as a negatively charged ion. As a result, there is a positively charged vacancy left behind. At the titania surface, either the oxygen ion reacts with an oxidizable carbon compound in the exhaust gas or two oxygen atoms or ions unite to form an oxygen molecule.

When the exhaust gases change to a composition corresponding to a lean mixture, the concentration of oxidizable carbon compounds is drastically reduced and an excess of oxygen appears in the exhaust gas. The oxygen concentration gradient reverses, and oxygen atoms are adsorbed on the titania surface and fill vacancies therein as was previously mentioned.

FIG. 6 illustrates the manner in which the ouput voltage of the sensor 10, connected in the circuit of FIG. 4, varies as a function of air/fuel ratio where this ratio changes from rich (below 14.7) to lean (above 14.7). When the mixture is rich, the sensor oxygen responsive metal oxide element 46 has a low resistance and the sensor output voltage is almost 100 percent, the percentage figure being the ratio of the actual output voltage to the input reference voltage multiplied by 100 percent. It may be seen that, with the temperature compensation provided by the titania thermistor element 48, there is very little variation in the sensor output voltage as a function of variation in temperatures between 350° C. and 850° C. Under rich conditions, the removal of oxygen from the titania structure to create new vacancies provides additional electrons from the titania atoms that may be used for the purpose of conduction. This explains the greatly increased conductivity of titania when exposed to exhaust gases produced by the combustion of rich mixtures. The opposite effect explains the very high resistance and low conductivity of the titania sensor element when exposed to exhaust gases produced by lean mixtures.

In the preferred form of the invention, the titania oxygen sensing element 46 is manufactured in accordance with the teachings of concurrently filed and commonly assigned U.S. patent application Ser. No. 5,425 filed in the names of A. Achari and one of the present inventors, and entitled "Improved Ceramic Element Sensor". A titania ceramic oxygen sensing element manufactured according to the teachings of the above-mentioned patent application may have very rapid response times with respect to variation of resistance resulting from changes in the partial pressure of oxygen in the gaseous medium to which the ceramic element is exposed. The titania thermistor 48, when constructed in accordance with the present invention, has a response time to variations of partial pressure of oxygen in the gaseous medium to which it is exposed that is much slower than that of the preferred oxygen sensing element 46.

In summary, the titania thermistor 48 is the second titania element in the circuit of FIG. 4 and has an electrical resistance that varies as a function of the second element temperature substantially identically electrically to the temperature variation of the titania oxygen sensing element 46, the first element in the circuit. The second titania element also has a substantially lengthened time rate of response to variations in the partial pressure of oxygen in the exhaust gases from an engine supplied with an air/fuel mixture switched from rich to lean, and vice versa.

The thermistor 48 resistance values plotted in FIG. 5 are shown to vary within a narrow band over the operating range of the exhaust gas sensor 10 when the air/fuel ratio of the mixture supplied to the engine in which the sensor is located varies cyclically between rich and lean conditions. Should the air/fuel mixture remain either rich or lean for a long period as compared to the rate of the cyclical variation, then the tendency of the thermistor 48 is to have its electrical resistance vary such that it approaches the resistance of the oxygen sensing element 46 for the temperature and rich or lean air/fuel mixture condition existing at the time.

In the prior art design of an exhaust gas sensor using a thermistor, the thermistor was constructed having a density approaching its theoretical density or, as preferred, a density greater than about 97% of its theoretical density. This density was found to be quite satisfactory for most purposes, but a difficulty was discovered with respect to the use of this thermistor in an exhaust gas sensor which might be operated under rich-mixture exhaust gas conditions for a period of several minutes and in the higher temperature portion of the sensor operating range. Under such conditions, the resistance of the very dense thermistor tends to approach that of the oxygen sensing element 46 as described above.

Unfortunately, it has been found that upon cooling of this very dense titania thermistor, the resistance of which has approached that of the titania oxygen sensing element at higher temperatures, the resistance changes only slightly. This small change is believed to be due to the change in temperature of the titania element in the rich-mixture exhaust gases. After the titania thermistor has cooled down, it then may be subjected to an exhaust gas produced by combustion of a lean air/fuel mixture. This immerses the titania thermistor in an excess of oxygen, but, because of its high density, it has been found that the titania thermistor may have a resistance change that is insufficient to cause it to produce a rich output voltage indication from the circuitry illustrated in FIG. 4. In other words, although the exhaust gas may be the product of a rich mixture, the circuitry under the previously described conditions may not indicate this condition properly.

The problem described above may be alleviated according to the present invention by the use of a titania thermistor material having a density in the range from 3.2 $g/cm^3$ to 3.8 $g/cm^3$. This corresponds to a range from about 76% to 90% of the theoretical density of titania, which is about 4.2 $g/cm^3$.

Figure 8:
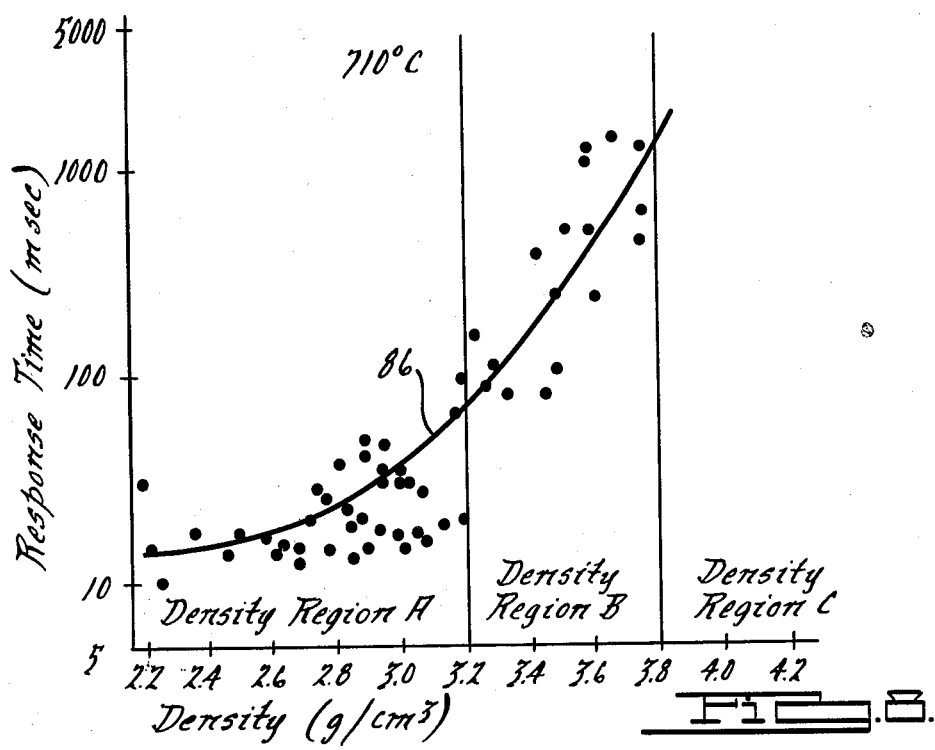
FIG. 8 is a graph that illustrates the response time of the titania material at 710° C. as a function of its density.

Reference is made to FIGS. 7 and 8 which show, respectively, the relationship between the resistance of titania and its response time versus the density of the titania ceramic material. In these FIGS. 7 and 8, there are shown curves 80, 82 and 86. Curve 80 illustrates the resistance of titania as a function of its density in the range of 2.2 to 3.8 $g/cm^3$, for the material when exposed to exhaust gases produced by combustion of a lean air/fuel mixture. Curve 82 shows the resistance for the titania material when exposed to exhaust gases resulting from rich air/fuel mixtures, and both curves 80 and 82 indicate such resistance values at a temperature of 710° C. The resistance measurements for curves 80 and 82 were obtained with air/fuel mixtures cycling four seconds rich and four seconds lean. It may be seen that in the density range from about 2.2 $g/cm^3$ to 3.2 $g/cm^3$, the resistance of the titania material under lean-mixture exhaust conditions is several orders or magnitude greater than that of the material under rich-mixture conditions. This is typical over the entire temperature operating range, as is indicated in FIG. 5 previously described.

It may be seen from FIG. 7 that in the region of density between 3.2 $g/cm^3$ and 3.8 $g/cm^3$, there is a pronounced decrease in the titania resistance in lean-mixture exhaust gases and a corresponding increase in resistance of titania material subjected to rich-mixture exhaust gases. In the region between the density of 3.8 g/cm³ and the theoretical density of 4.2 g/cm³, the resistance variation continues, but it is in this latter region that the aforementioned undesirable gas sensor operation may take place.

It has been found that the problem of the prior sensor design can be eliminated and good sensor operation obtained by utilization of a titania material having a density in the range from about 3.2 to 3.8 g/cm³. A density in the range from 3.4 to 3.8 g/cm³ is preferred and a density of about 3.7 g/cm³ is perhaps most appropriate for producing the titania thermistor variation 74 shown in FIG. 5. This variation produces the desirable results shown in FIG. 6 when the thermistor is used in association with the circuitry of FIG. 4. In contrast, the titania oxygen sensing element 46 has a preferred density of about 2.8 g/cm³, which is about 70% of theoretical density. The thermistor and oxygen sensing elements should have their densities selected to produce the most favorable results in their application, with considerabion being given to their cooperative relationship in the electrical circuit.

The curve 86, in FIG. 8, illustrates the titania material response time, at 710° C., to a change in exhaust gas compositions from rich to lean as a function of the titania density. It may be seen quite clearly that the response time, measured as the amount of time required for the output voltage from the circuit of FIG. 4 to change from 66% of its reference or input voltage value to 33% thereof, changes very rapidly over the density region of 3.2 to 3.8 g/cm³ and continues thereafter. In the density region from 3.8 to 4.2 g/cm³, the response time increases very dramatically as the theoretical density of 4.2 is approached. Titania at its theoretical density would have very littly ability to change in resistance in response to cyclical variations in the partial pressure of oxygen due to limited surface area for introduction of oxygen into the titania crystal structure.

Based upon the foregoing description of the invention, what is claimed is:

1. An improved exhaust gas sensor of the type having first and second titania ceramic elements with the electrical resistances which vary both as a function of temperature, over the temperature range from about 350° C. to about 850° C., and as a function of the partial pressure of oxygen in exhaust gases produced by the combustion of a rich or lean (with respect to stoichiometry) air/fuel mixture, the first and second titania elements having electrodes interconnected and adapted for receipt of an externally supplied voltage, the first titania element, when subjected to lean-mixture exhaust gases at temperatures within the temperature range, having a resistance about three orders of magnitude or more greater than its resistance at corresponding temperatures when subjected to rich-mixture exhaust gases, the second titania element having, when subjected to cycling lean-mixture/rich-mixture exhaust gases, varying resistance values intermediate the respective lean-mixture and rich-mixture exhaust gas resistances of the first titania element at corresponding temperatures over the temperature range, and the second titania element having a density between about 3.2 g/cm³ and about 3.8 g/cm³.

2. An improved exhaust gas sensor according to claim 1, wherein the second titania element, at about 850° C. and after exposure to rich-mixture exhaust gases for several minutes and when thereafter cooled to lower temperatures in the temperature range and exposed to lean-mixture exhaust gases, regains the intermediate resistance values.

* * * * *